United States Patent
Plumptre et al.

(10) Patent No.: US 11,471,602 B2
(45) Date of Patent: Oct. 18, 2022

(54) DOSE SETTING MECHANISM FOR PRIMING A DRUG DELIVERY DEVICE

(71) Applicant: Sanofi-Aventis Deutschland GmbH, Frankfurt am Main (DE)

(72) Inventors: David Aubrey Plumptre, Worcestershire (GB); James Alexander Davies, Warwickshire (GB); Christopher Jones, Worcestershire (GB); Robert Veasey, Warwickshire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 772 days.

(21) Appl. No.: 15/926,400

(22) Filed: Mar. 20, 2018

(65) Prior Publication Data
US 2018/0207364 A1 Jul. 26, 2018

Related U.S. Application Data

(63) Continuation of application No. 12/788,683, filed on May 27, 2010, now Pat. No. 9,950,116.
(Continued)

(30) Foreign Application Priority Data

Jul. 10, 2009 (EP) .................. 09009052

(51) Int. Cl.
*A61M 5/24* (2006.01)
*A61M 5/31* (2006.01)
*A61M 5/315* (2006.01)

(52) U.S. Cl.
CPC .......... *A61M 5/24* (2013.01); *A61M 5/31525* (2013.01); *A61M 5/3129* (2013.01);
(Continued)

(58) Field of Classification Search
CPC ................ A61M 5/24; A61M 5/31525; A61M 2005/2407; A61M 2005/2488;
(Continued)

(56) References Cited

U.S. PATENT DOCUMENTS

| | | |
|---|---|---|
| 533,575 A | 2/1895 | Wilkens |
| 3,302,462 A | 2/1967 | Pursell |

(Continued)

FOREIGN PATENT DOCUMENTS

| | | |
|---|---|---|
| DE | 9301334 U1 | 4/1993 |
| DE | 19730999 C1 | 12/1998 |

(Continued)

OTHER PUBLICATIONS

Machine Design, Penton Media, vol. 65, No. 11 (1993) p. 36 "Standard Compression Springs Save Space".

*Primary Examiner* — Lauren P Farrar
*Assistant Examiner* — Hamza A Darb
(74) *Attorney, Agent, or Firm* — McCarter & English, LLP

(57) ABSTRACT

A method and system for providing a drug delivery device. The drug delivery device comprises a dose setting mechanism comprising a spindle and a cartridge holder coupled to the dose setting mechanism. The cartridge holder comprising a cartridge having a movable bung at one end of the cartridge. The cartridge holder must be rotated before a dose may set with the dose setting mechanism.

16 Claims, 7 Drawing Sheets

Related U.S. Application Data

(60) Provisional application No. 61/182,828, filed on Jun. 1, 2009.

(52) U.S. Cl.
CPC ....... *A61M 5/3146* (2013.01); *A61M 5/31543* (2013.01); *A61M 5/31551* (2013.01); *A61M 2005/2407* (2013.01); *A61M 2005/2488* (2013.01); *A61M 2005/2492* (2013.01)

(58) Field of Classification Search
CPC ........ A61M 2005/2492; A61M 5/3129; A61M 5/3146; A61M 5/31543; A61M 5/31551
See application file for complete search history.

(56) References Cited

U.S. PATENT DOCUMENTS

| | | | |
|---|---|---|---|
| 5,092,842 A * | 3/1992 | Bechtold | A61M 5/20 604/135 |
| 5,226,895 A * | 7/1993 | Harris | A61J 1/1406 604/208 |
| 5,279,586 A | 1/1994 | Balkwill | |
| 5,304,152 A | 4/1994 | Sams | |
| 5,320,609 A | 6/1994 | Haber et al. | |
| 5,383,865 A | 1/1995 | Michel | |
| 5,423,752 A | 6/1995 | Haber et al. | |
| 5,480,387 A | 1/1996 | Gabriel et al. | |
| 5,505,704 A | 4/1996 | Pawelka et al. | |
| 5,514,097 A | 5/1996 | Knauer | |
| 5,582,598 A | 12/1996 | Chanoch | |
| 5,584,815 A | 12/1996 | Pawelka et al. | |
| 5,591,136 A | 1/1997 | Gabriel | |
| 5,626,566 A | 5/1997 | Petersen et al. | |
| 5,674,204 A | 10/1997 | Chanoch | |
| 5,688,251 A * | 11/1997 | Chanoch | A61M 5/3146 222/309 |
| 5,792,117 A | 8/1998 | Brown | |
| 5,820,602 A | 10/1998 | Kovelman et al. | |
| 5,921,966 A | 7/1999 | Bendek et al. | |
| 5,938,642 A | 8/1999 | Burroughs et al. | |
| 5,961,495 A | 10/1999 | Walters et al. | |
| 6,004,297 A | 12/1999 | Steenfeldt-Jensen et al. | |
| 6,090,080 A | 7/2000 | Jost et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,899,698 B2 | 5/2005 | Sams | |
| 6,936,032 B1 * | 8/2005 | Bush, Jr. | A61M 5/31551 604/187 |
| 7,241,278 B2 | 7/2007 | Moller | |
| 7,811,263 B2 | 10/2010 | Burren et al. | |
| 8,361,036 B2 | 1/2013 | Moller et al. | |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0127858 A1 | 7/2004 | Bendek et al. | |
| 2004/0162528 A1 | 8/2004 | Horvath et al. | |
| 2004/0186437 A1 | 9/2004 | Frenette et al. | |
| 2004/0210199 A1 | 10/2004 | Atterbury et al. | |
| 2004/0236285 A1 | 11/2004 | Fisher et al. | |
| 2004/0267207 A1 | 12/2004 | Veasey et al. | |
| 2005/0113765 A1 | 5/2005 | Veasey et al. | |
| 2005/0137571 A1 | 6/2005 | Hommann | |
| 2006/0153693 A1 | 7/2006 | Fiechter et al. | |
| 2006/0258988 A1 | 11/2006 | Keitel et al. | |
| 2007/0016142 A1 * | 1/2007 | Burren | A61M 5/315 604/207 |
| 2007/0016143 A1 * | 1/2007 | Miller | A61M 5/31583 604/208 |
| 2007/0021718 A1 | 1/2007 | Burren et al. | |
| 2008/0027397 A1 * | 1/2008 | DeRuntz | A61M 5/31558 604/220 |
| 2008/0077095 A1 | 3/2008 | Kirchhofer | |
| 2008/0208123 A1 | 8/2008 | Hommann | |
| 2009/0227959 A1 | 9/2009 | Hirschel et al. | |
| 2009/0275916 A1 | 11/2009 | Harms et al. | |

FOREIGN PATENT DOCUMENTS

| | | | |
|---|---|---|---|
| DE | 29818721 U1 | 3/2000 | |
| DE | 102005063311 A1 | 8/2006 | |
| DE | 102005060928 A1 | 6/2007 | |
| DE | 102006038123 A1 | 2/2008 | |
| DE | 102007026083 A1 | 11/2008 | |
| EP | 0897728 A1 | 2/1999 | |
| EP | 0937471 A2 | 8/1999 | |
| EP | 0937472 A2 | 8/1999 | |
| EP | 0937476 A2 | 8/1999 | |
| EP | 1541185 A1 | 6/2005 | |
| EP | 1776975 A2 | 4/2007 | |
| EP | 1923084 A1 | 5/2008 | |
| EP | 2054111 A1 * | 5/2009 | A61M 5/2448 |
| GB | 2443390 A | 5/2008 | |
| WO | 9218180 A1 | 10/1992 | |
| WO | 9307922 A1 | 4/1993 | |
| WO | 9623973 A1 | 8/1996 | |
| WO | 9639214 A1 | 12/1996 | |
| WO | 9710864 A1 | 3/1997 | |
| WO | 9938554 | 8/1998 | |
| WO | 9903520 A1 | 1/1999 | |
| WO | 0110484 | 2/2001 | |
| WO | 0119434 A1 | 3/2001 | |
| WO | 03080160 A1 | 10/2003 | |
| WO | 2004020028 A1 | 3/2004 | |
| WO | 2004064902 A1 | 8/2004 | |
| WO | 2004078241 A1 | 9/2004 | |
| WO | 2004078242 A2 | 9/2004 | |
| WO | 2004078293 A1 | 9/2004 | |
| WO | 2005018721 A1 | 3/2005 | |
| WO | 2005021072 A1 | 3/2005 | |
| WO | 2005044346 A2 | 5/2005 | |
| WO | 2005123159 A2 | 12/2005 | |
| WO | 2006024461 A1 | 3/2006 | |
| WO | 2006058883 A2 | 6/2006 | |
| WO | 2006079481 A1 | 8/2006 | |
| WO | 2006089767 A1 | 8/2006 | |
| WO | 2006114395 A1 | 11/2006 | |
| WO | 2006125328 A1 | 11/2006 | |
| WO | 2007017052 A1 | 2/2007 | |
| WO | 2007067889 A1 | 6/2007 | |
| WO | 2008031235 A1 | 3/2008 | |
| WO | 2008074897 A1 | 6/2008 | |
| WO | 2008116766 A1 | 10/2008 | |
| WO | 2008128373 A1 | 10/2008 | |

* cited by examiner

DOSE SETTING MECHANISM FOR PRIMING A DRUG DELIVERY DEVICE

CROSS REFERENCE TO RELATED APPLICATIONS

The present application is continuation application of U.S. patent application Ser. No. 12/788,683 filed May 5, 2017 which claims priority to U.S. Provisional Patent Application Ser. No. 61/182,828 filed Jun. 1, 2009, which claims priority to European Patent Application No. 09009052.3 filed Jul. 10, 2009. The entire disclosure contents of these applications are herewith incorporated by reference into the present application.

BACKGROUND

Field of the Present Patent Application

The present patent application is generally directed to drug delivery devices. More particularly, the present patent application is generally directed to drug delivery devices, such as pen type drug delivery devices. Such devices provide for self administration of medicinal product from a multi-dose cartridge and permit a user to set the delivery dose. The present application may find application in both resettable (i.e., reusable) and non-resettable (i.e., non-reusable) type drug delivery devices. However, aspects of the invention may be equally applicable in other scenarios as well.

Background

Pen type drug delivery devices have application where regular injection by persons without formal medical training occurs. This is increasingly common among patients having diabetes where self-treatment enables such patients to conduct effective management of their disease.

In certain types of medication delivery devices, such as pen type devices, cartridges of medication are used. These cartridges are housed in a cartridge holder or cartridge housing. Such cartridges include a bung or stopper at one end. At the other end of the cartridge, the cartridge may comprise a pierceable seal. To dispense a dose of medication from such a cartridge, the medication delivery device has a dose setting mechanism that uses a spindle to move in a distal direction towards the cartridge and to press a distal end of the spindle against the bung. This expels a certain set or preselected dose of medication from the cartridge. In order to insure dose accuracy, it is important that the distal end of the spindle remains on the bung of the cartridge before, during and after injection of a dose of medicament.

One perceived disadvantage of certain known medication delivery devices is that because of the various tolerance differences that may occur during manufacturing (e.g., tolerance differences that may arise during component molding) of the various parts making up the drug delivery device and the desire to not pre-load the bung axially in the assembled device, there may be a gap between the end of the spindle and the cartridge bung after the medication delivery device has been assembled. In other words, when initially assembled, the cartridge (and hence cartridge bung) may not be in contact with the distal end of the spindle. Therefore, if a user using the drug delivery device for the first time dials a dose, the actual dose received may be equal to the dialed dose less the initial gap between the distal end of the spindle and cartridge bung. The air gap between the cartridge bung and distal end of the spindle may be equivalent to a dose that causes the received dose that is outside preferred dose accuracy limits. For example, this air gap may be equivalent to the loss of between 0 and 10 units (i.e., 0-0.14 milliliters) of drug product on the first dose. There is, therefore, a general need to take these perceived issues into consideration when designing either resettable or non-resettable drug delivery devices, such as pen type drug delivery devices.

SUMMARY

According to an exemplary arrangement, a drug delivery device comprises a dose setting mechanism comprising a spindle. A cartridge holder is coupled to the dose setting mechanism. The cartridge holder comprises a cartridge having a movable bung at one end of the cartridge. The cartridge holder is rotated before a dose may set with the dose setting mechanism.

According to another arrangement, a priming mechanism for a drug delivery device comprises a dose setting mechanism. The dose setting mechanism comprises a spindle and a dose dial sleeve. A cartridge holder comprises a cartridge comprising a movable bung and a pierceable seal. A coupling part connects the cartridge holder to the dose dial sleeve. A spindle nut, rotationally coupled to the coupling part, couples the cartridge holder to the spindle. When the cartridge holder is rotated with respect to the dose setting mechanism, the spindle nut is rotated and the coupling part moves the spindle into an abutting engagement with the bung.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which.

DETAILED DESCRIPTION

Figure 1:
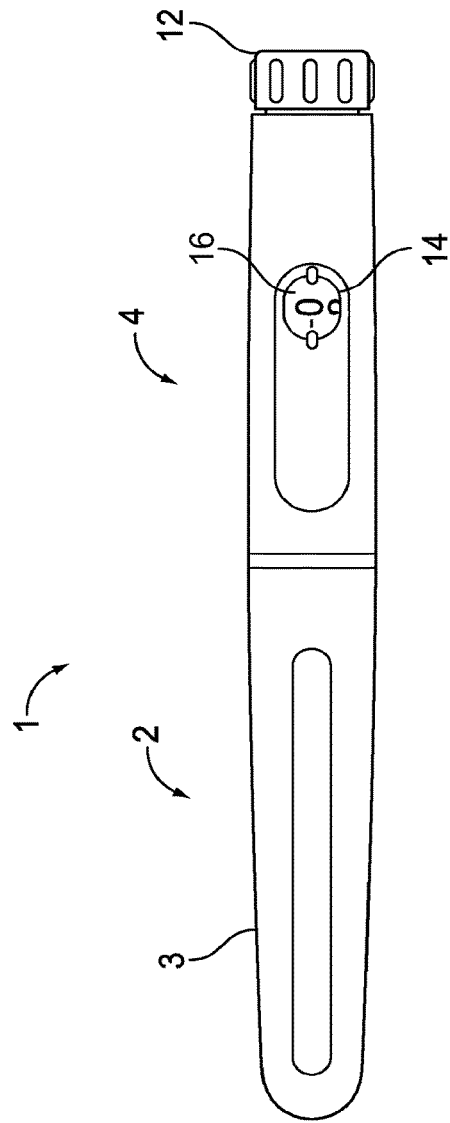
FIG. 1 illustrates an arrangement of a drug delivery device in accordance with the one aspect of the present invention.

Referring to FIG. 1, there is shown a drug delivery device 1 in accordance with an exemplary arrangement. The drug delivery device 1 comprises a housing having a first cartridge retaining part 2, and a dose setting mechanism 4. The drug delivery device may be a resettable drug delivery device (i.e., a reusable device) or alternatively a non-resettable drug delivery device (i.e., a non-reusable device). A first end of the cartridge retaining part 2 and a second end of the dose setting mechanism 4 are secured together by connecting features. For non-resettable devices, these connecting features would be permanent and non-reversible. For resettable devices, these connecting features would be releasable.

In this illustrated arrangement, the cartridge housing 2 is secured within the second end of the dose setting mechanism 4. A removable cap 3 is releasably retained over a second end or distal end of a cartridge retaining part or cartridge housing. The dose setting mechanism 4 comprises a dose dial grip 12 and a window or lens 14. A dose scale arrangement 16 is viewable through the window or lens 14. To set a dose of medication contained within the drug delivery device 1, a user rotates the dose dial grip 12 such that a dialed dose will become viewable in the window or lens 14 by way of the dose scale arrangement 16.

Figure 2:
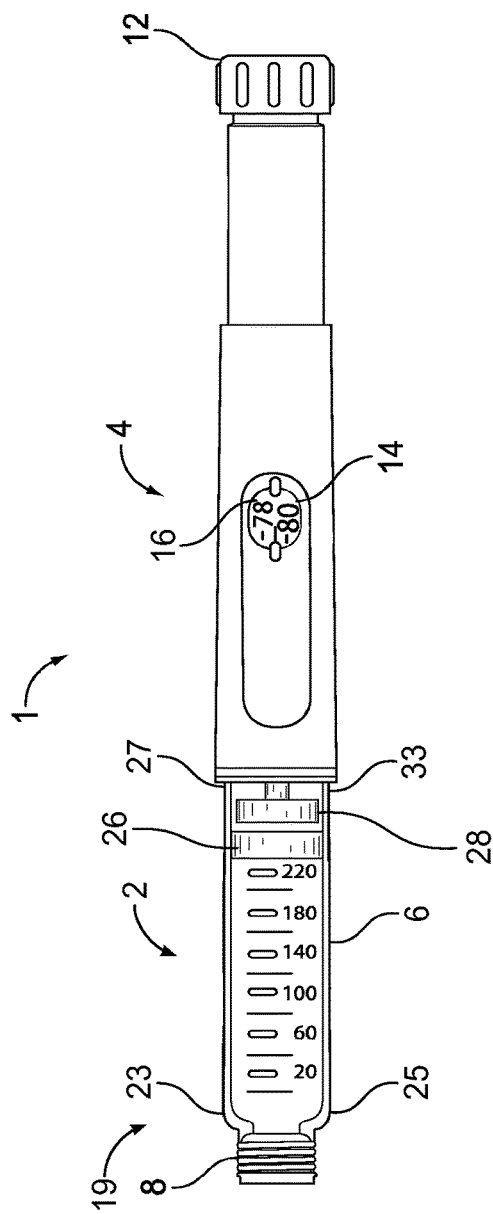
FIG. 2 illustrates the drug delivery device of FIG. 1 with a cap removed and with a dose having been selected.

FIG. 2 illustrates the medical delivery device 1 of FIG. 1 with the cover 3 removed from a distal end 19 of the medical delivery device 1. This removal exposes the cartridge housing 6. As illustrated, a cartridge 25 from which a number of doses of a medicinal product may be dispensed, is provided in the cartridge housing 6.

Preferably, the cartridge 25 contains a type of medicament that can be administered relatively often, such as once or more times a day. One such medicament is either long acting or short acting insulin or insulin analog. The cartridge 25 comprises a bung or stopper 26 that is retained near a second end or a proximal end 33 of the cartridge 25. The medical delivery device also comprises a driver having a spindle 28. As discussed above, before the device is primed, there may or may not be a gap between the end of the spindle and the cartridge bung.

The cartridge housing 6 has a distal end 23 and a proximal end 27. Preferably, the cartridge distal end 23 of the cartridge housing 6 comprises a groove 8 for attaching a removable needle assembly. However, other needle assembly connection mechanisms could also be used. If the drug delivery device 1 comprises a resettable device, the cartridge proximal end 27 is removably connected to the dose setting mechanism 4. In one preferred embodiment, cartridge housing proximal end 27 is removably connected to the dose setting mechanism 4 via a bayonet connection.

However, as those of ordinary skill in the art will recognize, other types of removable connection methods such as threads, partial threads, ramps and detents, snap locks, snap fits, and luer locks may also be used.

As previously mentioned, the dose setting mechanism 4 of the drug delivery device illustrated in FIG. 2 may be utilized as a reusable drug delivery device. (i.e., a drug delivery device that can be reset) Where the drug delivery device 1 comprises a reusable drug delivery device, the cartridge 25 is removable from the cartridge housing 6. The cartridge 25 may be removed from the device 1 without destroying the device 1 by merely having the user disconnect the dose setting mechanism 4 from the cartridge housing 6.

In use, once the cap 3 is removed, a user can attach a suitable needle assembly to the groove 8 provided at the distal end 23 of the cartridge housing 6. Such needle assembly may be, for example, screwed onto a distal end 23 of the housing 6 or alternatively may be snapped onto this distal end 23. After use, the replaceable cap 3 may be used to re-cover the cartridge housing 6. Preferably, the outer dimensions of the replaceable cap 3 are similar or identical to the outer dimensions of the dose setting mechanism 4 so as to provide an impression of a unitary whole when the replaceable cap 3 is in position covering the cartridge housing 6 when the device is not in use.

In accordance with an exemplary arrangement, it may be beneficial to force a user to prime the drug delivery device of FIGS. 1 and 2 before the user dials and injects the first dose. In order to achieve this forced priming, as will be discussed in greater detail below, the drug delivery device 1 preferably forces a user to prime the device before they are permitted to select the first dose.

The process of forcing a user to prime the cartridge before they can select and dispense the first dose reduces a potential risk of injecting the prime dose. The idea of forced priming is particularly advantageous for disposable devices where there is oftentimes a gap between a distal end of the spindle and the cartridge bung before the device is used. This gap is a consequence of the tolerances associated with the assembled parts as well as the desire not to pre-load the bung axially in the assembled device.

If the device is designed so that this gap between a distal end of the spindle and the bung is removed (i.e., the device primed) before the user is able to dial a dose, then this is advantageous. In one preferred arrangement, the drug delivery device achieves this by the user rotating the cartridge holder relative to the housing in order to both prime the device and also to unlock the number sleeve so the user can subsequently rotate the dose dial sleeve to set the first dose. Preferably, once the device has been primed, the cartridge holder is locked rotationally and therefore cannot be rotated with respect to the dose setting mechanism.

Figure 3:
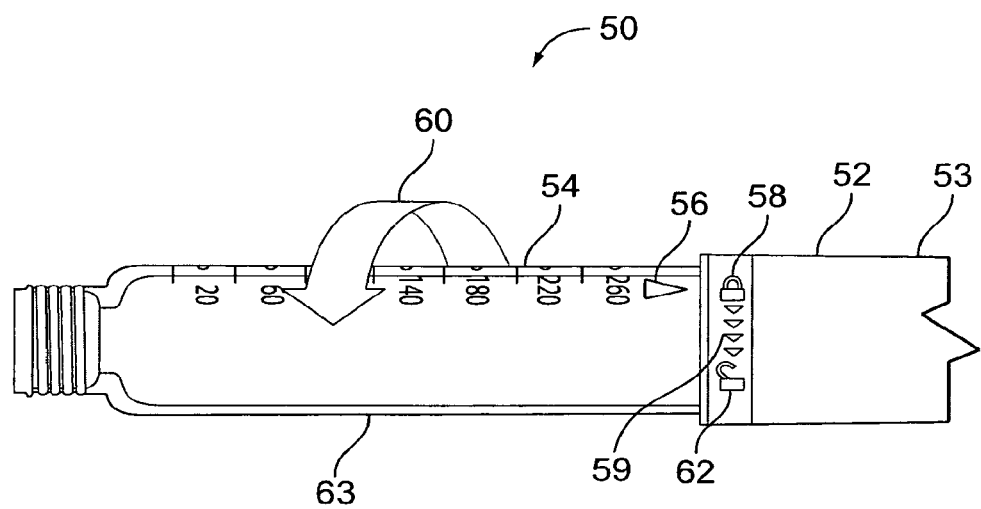
FIG. 3 illustrates a close up view of a drug delivery device before a priming step, such as the drug delivery device illustrated in FIG. 1.
Figure 4:
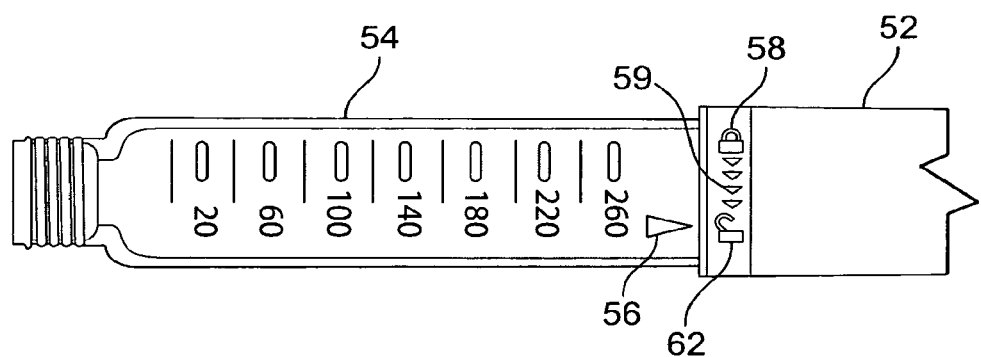
FIG. 4 illustrates a close up view of the drug delivery device illustrated in FIG. 3 after completion of a priming step.

FIG. 3 illustrates a close up view of a drug delivery device 50 before a priming step, such as the drug delivery device 1 illustrated in FIG. 1. FIG. 4 illustrates a close up view of the drug delivery device 50 illustrated in FIG. 3 after completion of a priming step. As illustrated, the drug delivery device 50 comprises a dose setting mechanism 52 coupled to a cartridge housing 54. Where the drug delivery device 50 comprises a re-settable drug delivery device, this coupling mechanism comprises a releasable coupling mechanism (i.e., a thread, a bayonet lock, a luer lock, a snap fit or snap lock, etc.) Where the drug delivery device 50 comprises a non-resettable drug delivery device (i.e., a disposable drug delivery device), this coupling this coupling mechanism comprises a non-reversible coupling mechanism.

In this preferred arrangement of drug deliver device 50, the dose setting mechanism 52 comprises various markings and indications along an outer surface 53. As can be seen in this arrangement, this marking comprises a marking indicating a locked position (i.e., un-primed state) 58 and a marking indicating an unlocked position (i.e., primed state)

62. In addition, various intermediate markings 59 are provided between the locked and unlocked position markings 58, 62, respectively.

Figure 5:
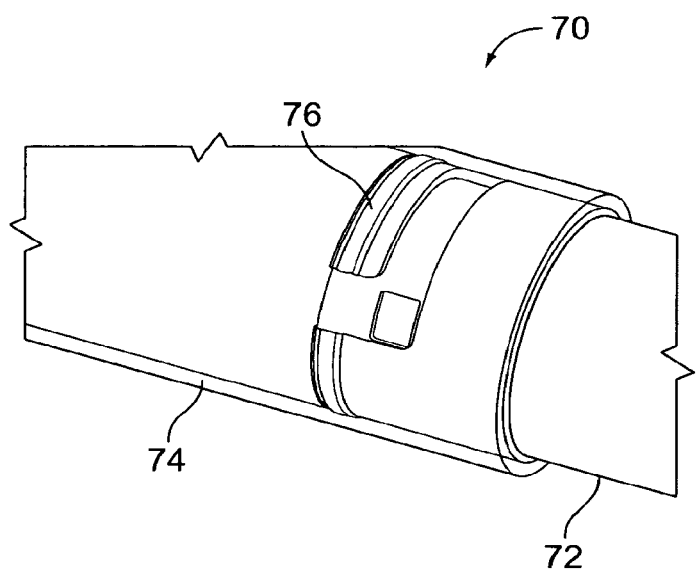
FIG. 5 illustrates a close up view of a connection between a dose setting mechanism and cartridge housing of a drug delivery device in a non-priming state, such as drug delivery device illustrated in FIGS. 3 and 4.

In addition, the cartridge housing 54 comprises markings along its outer surface 63 and these markings include a positional indicator (i.e., an arrow) 56 that is used to indicate the relative position of the cartridge housing 54 with respect to the outer surface 53 of the dose setting mechanism 52. In this preferred arrangement, to prime the drug delivery device 50, the cartridge housing 54 is rotated in direction of arrow 60. Preferably, the cartridge housing 54 is rotated in the direction of arrow 60 with respect to the dose setting mechanism 52 so that the arrow 56 moves from the locked marking 58 and then aligns with the unlocked designation 62, as shown in FIG. 4. In this final position, the drug delivery device 50 now resides in a primed state. That is, the spindle contained in the dose setting mechanism 52 now resides adjacent or abuts the bung provided in the cartridge of the cartridge housing 54. In addition, in a preferred arrangement, the drug delivery device 50 is also now unlocked so that the dose setting mechanism 52 may now be used to set a dose (as illustrated in FIG. 2). Most preferably, in this final position, the cartridge holder 54 is also rotationally locked and can therefore no longer be rotated with respect to the dose setting mechanism 52. FIG. 5 illustrates a close up view of a connection between a dose setting mechanism and cartridge housing of a drug delivery device 70, such as drug delivery device 50 illustrated in FIGS. 3 and 4. In FIG. 5, the drug delivery device 70 is in a pre-primed state. Therefore, with the drug delivery device illustrated in FIG. 5, a user could not set a dose until the device is primed. As illustrated, the dose setting mechanism 74 is rotationally coupled to the cartridge housing 72. In this arrangement, the cartridge housing 72 comprises a rib 76 that engages with an internally formed cavity on an inner surface of the dose setting mechanism 74. This configuration allows for relative rotational movement only between the dose setting mechanism 74 and the cartridge housing 76 and no axial movement. This rotational relative movement occurs when the cartridge holder 72 is rotated from the locked position (i.e., FIG. 5) to the unlocked position (i.e., FIG. 6).

Figure 6:
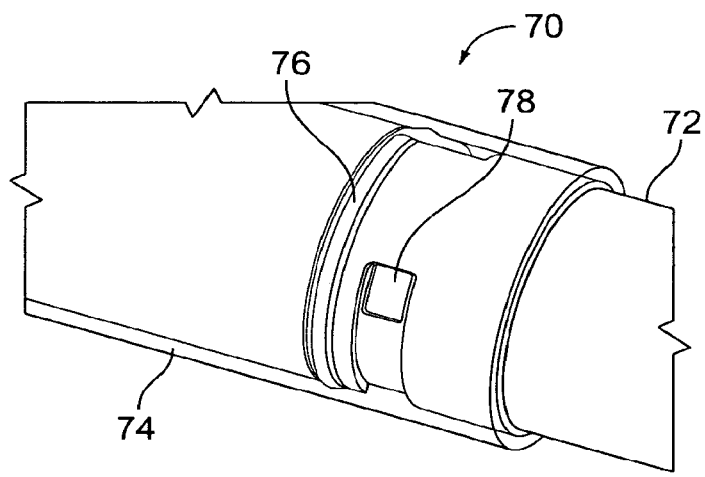
FIG. 6 illustrates a close up view of the connection between the dose setting mechanism and the cartridge illustrated in FIG. 5, in a priming state.
Figure 7:
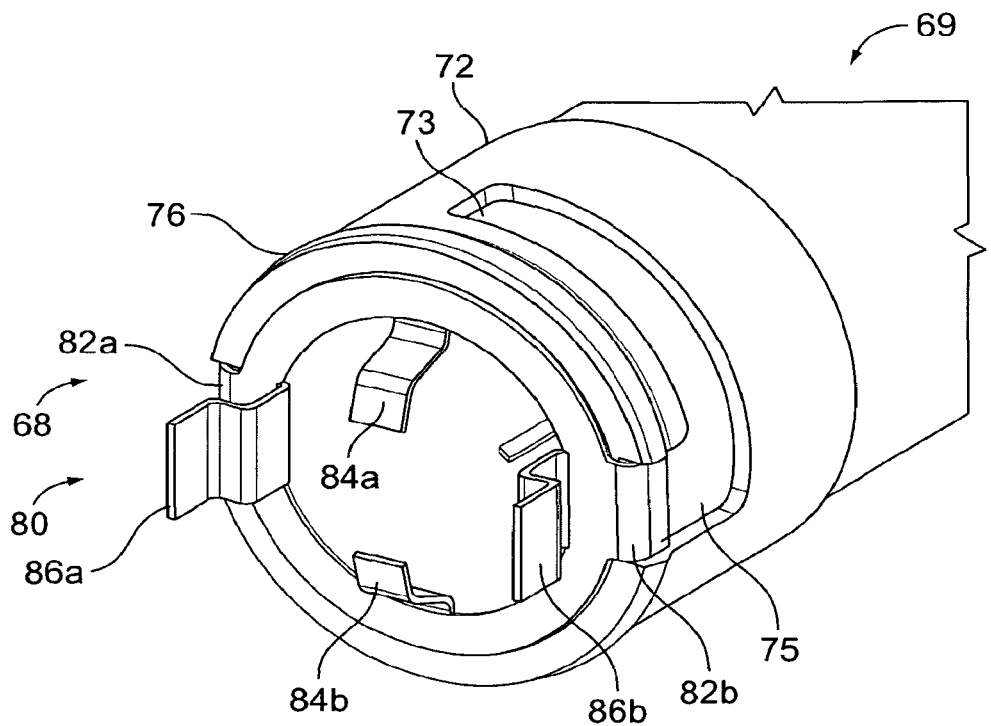
FIG. 7 illustrates a close up view of a proximal end of the cartridge housing illustrated in FIGS. 5 and 6, including a coupling part

FIG. 7 illustrates a close up view of a proximal end 68 of the cartridge housing 72 illustrated in FIGS. 5 and 6. FIG. 7 also illustrates a coupling part 80 that may be used to couple the cartridge housing 72 to a dose setting mechanism, such as the dose setting mechanism 74 illustrated in FIGS. 5 and 6. In this preferred arrangement, this cartridge housing 72 comprises an L shaped cavity 73 provided along a first outer surface 75 of the cartridge housing 72. As described with respect to FIGS. 5 and 6 and as will be described in greater detail below, this cavity 73 is used to engage a portion of a coupling part so as to allow relative rotation between the cartridge holder 72 and the dose setting mechanism.

In this preferred arrangement, coupling part 80 comprises a thin metal pressing. However, those of ordinary skill will recognize that alternative coupling part arrangements may also be used. In this preferred arrangement, the coupling part 80 comprises a first set of axial projecting members 82a, 82b that project in an axial direction towards the distal end 69 of the cartridge housing 72. These projecting members 82a, 82b rotationally affix or engage a first portion 75 of the cavity 73. In addition, the coupling part 80 rotationally couples to a spindle nut and therefore a spindle of a dose setting mechanism and also acts upon a dose dial sleeve of the dose setting mechanism.

The coupling part 80 further comprises a second set of axial projecting members 86a, 86b. This second set of projecting members 86a, 86b extend in a proximal direction away from the proximal end 68 of the cartridge housing 72. This second set of projecting members 86a, 86b engage a portion of the dose setting mechanism, specifically an inner housing of the dose setting mechanism. As described below, the coupling part 80 further comprises two inwardly extending arms 84a, 84b that engage a spindle nut of the dose setting mechanism.

Figure 8:
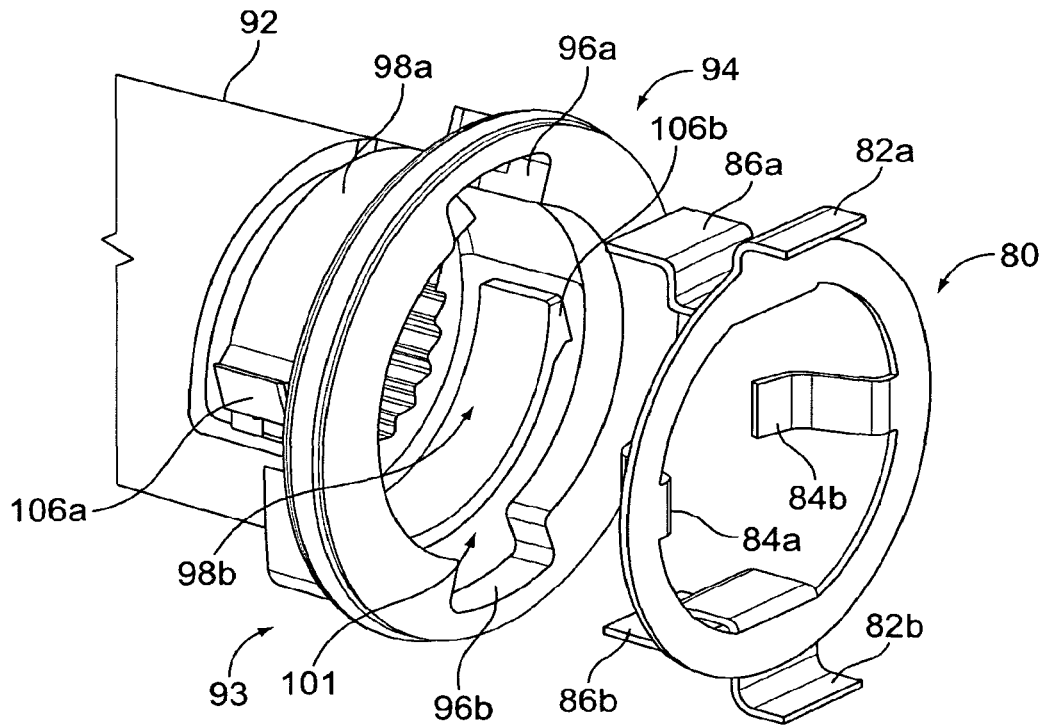
FIG. 8 illustrates how the coupling part illustrated in FIG. 7 may be used to engage a dose dial sleeve of a dose setting mechanism, such as the dose setting mechanism illustrated in FIGS. 5 and 6.

FIG. 8 illustrates how the coupling part 80 illustrated in FIG. 7 may be used to engage an inner housing 92 of a dose setting mechanism, such as the dose setting mechanism illustrated in FIGS. 5 and 6. As illustrated, the inner housing 92 comprises a first and a second flexible locking elements 98a, 98b located near a distal end 93 of the inner housing 92. Also near this distal end 93 is a circular shaped housing portion 94. This housing portion 94 defines a cavity portion 101 having an inner surface and along this inner surface there are two internally radially directed recesses 96a and 96b.

During assembly, the coupling part 80 will be positioned to slide into the cavity 101 of the housing portion 94 such that the second set of protruding members 86a, 86b of the coupling part 80 slide through recesses 96a, 96b of the housing portion 94, respectively. The second members 86a, 86b will then be positioned to reside over an external surface of the inner housing flexible elements 98a, 98b, respectively. In this position, the drug delivery device will not be primed but rather the dose dial sleeve 103 will be locked out and prevented from rotating. As such, a user of such a drug delivery device will be prevented from selecting a dose, that is, the user will be prevented from rotating the dose dial sleeve 103 before the user has under taken a drug delivery device priming step.

Figure 9:
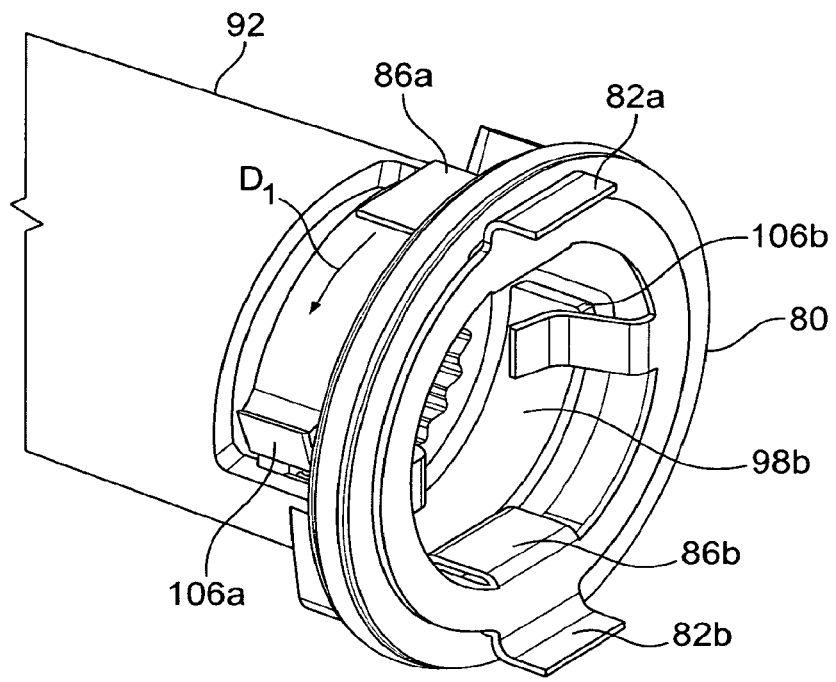
FIG. 9 illustrates the coupling part illustrated in FIG. 8 in a non-primed state.
Figure 10:
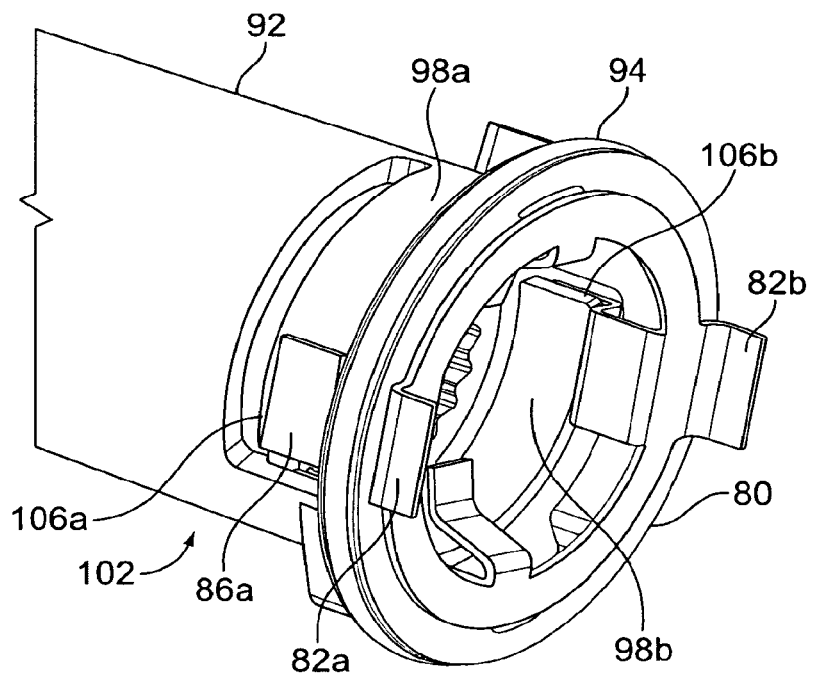
FIG. 10 illustrates the coupling part illustrated in FIG. 9 in a primed state.
Figure 11:
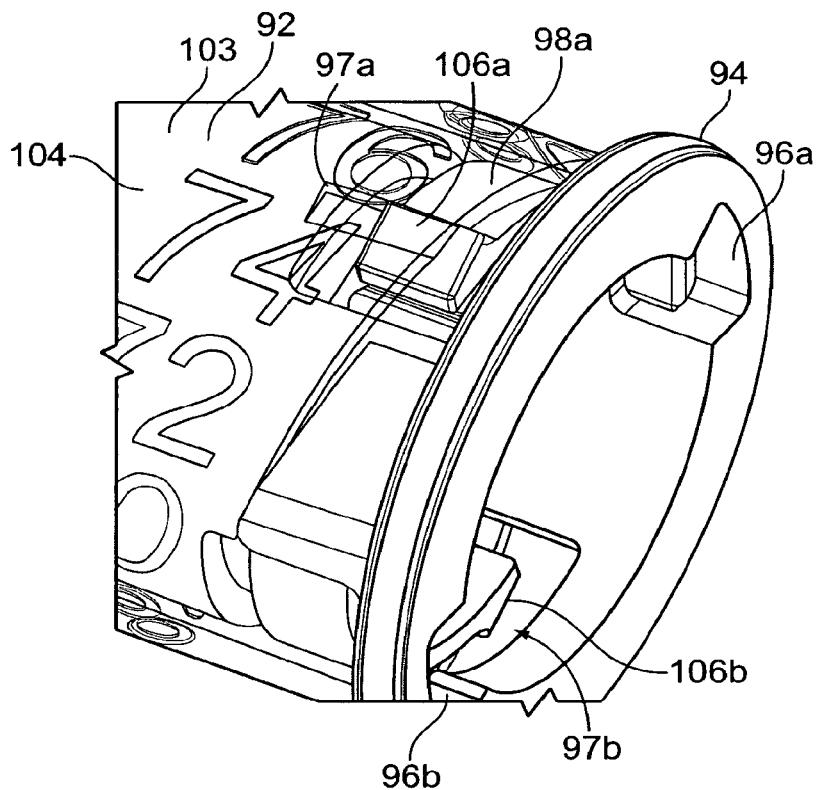
FIG. 11 illustrates a close up view of the stop faces provided along the distal end of the dose dial sleeve illustrated in FIG. 10
Figure 12:
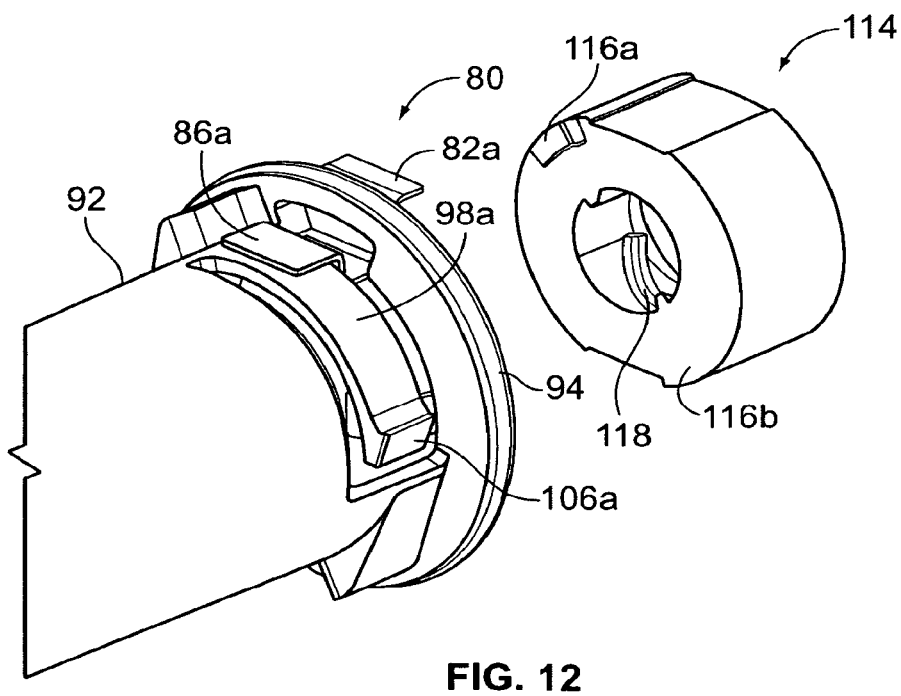
FIG. 12 illustrates a spindle nut that may be used to couple the coupling part to a dose setting member and to a cartridge housing.

FIG. 9 illustrates the coupling part 80 engaged with the distal end 93 of the inner housing 92. As illustrated, the coupling part 80 is in an initial position or in a non-primed state, before device priming occurs. In this initial position, the set of protruding elements 86a, 86b reside over the surface of the flexible elements 96a, and 96b, respectively. Therefore, when a cartridge holder is connected to the housing and is rotated (as illustrated in FIGS. 4 and 5), the coupling part 80 also rotates. As the coupling part 80 is rotated in the direction of arrow D1, the first set of protruding elements 86a, 86b rotate over the flexible locking elements 98a, 98b and end up releasing these flexible locking elements, and therefore stop faces 106a, 106 from the dose dial sleeve. FIG. 10 illustrates the coupling part 80 and inner housing 92 after rotating the coupling part to release the flexible locking elements and thereby completing of the priming step. As illustrated, the coupling part 80 has been rotated to a final or stop position 102 and the coupling part 80 has now been is rotated less than 360 degrees so as to push the inner housing flexible elements 98a, 98b radially inward. This releases the inner housingstop faces 106a, 106b, from the dose dial sleeve 103. FIG. 11 illustrates a close up view of the stop faces 106a, 106b provided along the distal end of the inner housing 92. The dose dial sleeve 103 is also illustrated with a scale arrangement 104 provided along an outer surface of this dose dial sleeve 103. The dose dial sleeve 103 has mating stop faces 97a, 97b that engage with stop faces 96a, 96b on the inner housing A spindle nut 114 is coupled to the coupling part 80 so that when the coupling part 80 rotates the spindle nut 114 rotates to drive a spindle 124 distally. As illustrated, this spindle nut 114 is circular in shape and comprises a first and a second helical ramp 116a, 116b. The spindle nut 114 further comprises a circular cavity having a male groove member 118. Once assembled, the spindle nut 114 is rotationally coupled to the coupling part 80 so that when a cartridge holder is coupled to a dose setting member and the cartridge holder is rotated, the spindle nut 114 rotates along with the cartridge holder. The first and second helical ramps 116a, 116b serve to drive the spindle nut 114 in a distal direction (i.e., towards the injection site) when the cartridge holder is rotated. Where the spindle nut 114 is used in drug delivery device comprising a non-resettable drug delivery device, these helical ramps lock the cartridge holder rotationally at the end of the priming step. However, where the spindle nut is used in a resettable drug delivery device, the helical ramps are detented so as to allow the cartridge housing 72 to be rotated back and removed to enable a new cartridge to be fitted.

The height of the helical ramps 116a, 116b help to offset any slack in the drive mechanism that drives the spindle of the dose setting mechanism forwards to dispense a dose. In this manner, rotating the cartridge holder is generally equivalent to pressing on a dose button of the dose setting mechanism so as to take up slack in the drive mechanism.

Figure 13:
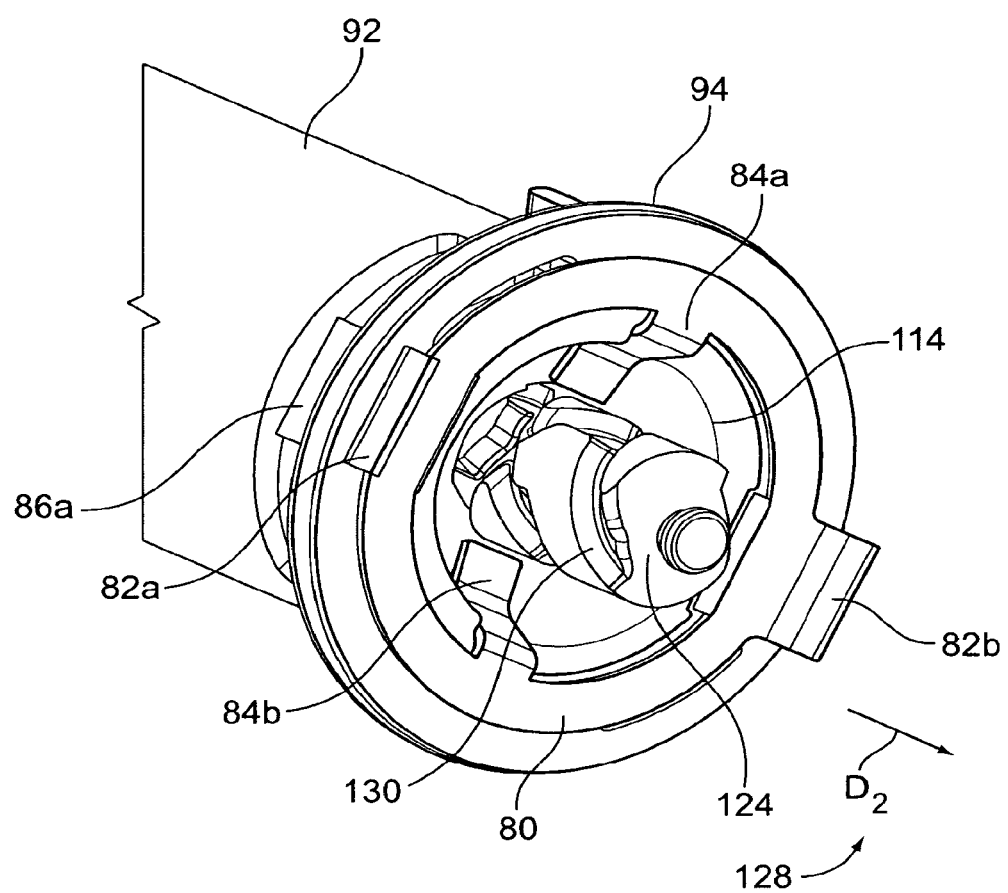
FIG. 13 illustrates the spindle nut coupled to the coupling part and dose dial sleeve of a dose setting mechanism.

FIG. 13 illustrates the spindle nut 114 coupled to the coupling part 80 and inner housing 92 of a dose setting mechanism. In this illustration, the coupling part 80 is rotated by the cartridge holder (not illustrated). This in turn rotates the spindle nut 114. As illustrated, this spindle has at least two overlapping grooves. Preferably, one of these grooves 130 is engaged with a portion of the drug deliver device and could be either helical or axially extending along its length.

Because in one arrangement the spindle 124 is threaded to a portion of the drug delivery device, as the spindle nut 114 rotates, it advances the spindle 124 axially in the distal direction D2 128 so as to prime the drug delivery device. The rotation of the cartridge housing, as mentioned, also unlocks the dose dial sleeve 103 to allow a user to now sett a first dose of medication for the drug delivery device.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A priming mechanism for a drug delivery device, said priming mechanism comprising:
   a dose setting mechanism comprising
      a spindle; and
      a dose dial sleeve;
   a cartridge holder, said cartridge holder comprising a cartridge, said cartridge comprising a movable bung near a proximal end of said cartridge;
   a coupling part connecting said cartridge holder to said dose dial sleeve of said dose setting mechanism, and
   a spindle nut rotationally coupled to said coupling part, said spindle nut coupling said cartridge holder to said spindle of said dose setting mechanism such that when said cartridge holder is rotated with respect to said dose setting mechanism, said spindle nut is rotated along with said cartridge holder with respect to said dose setting mechanism and at a same time driven in a distal direction with respect to said dose setting mechanism, and advances said spindle axially in the distal direction with respect to said dose setting mechanism such that said spindle nut moves said spindle into an abutting engagement with said bung so as to prime the drug delivery device.

2. The invention of claim 1 wherein said coupling part is configured to unlock said dose dial sleeve so that said dose dial sleeve becomes free to rotate to set a dose.

3. The invention of claim 1 wherein said coupling part comprises a thin metal pressing.

4. The invention of claim 1 wherein said coupling part comprises a rigid coupling component.

5. The invention of claim 1 wherein said dose setting mechanism further comprises at least one flexible locking element, and
   wherein when said cartridge holder is rotated with respect to said dose setting mechanism, said coupling part also rotates to thereby release said at least one flexible locking element and allow said dose dial sleeve to rotate and allow a user of said drug delivery device to set a dose.

6. The invention of claim 1 wherein said spindle nut comprises a plurality of helical ramps, said plurality of helical ramps configured to drive said spindle nut in said distal direction with respect to said dose setting mechanism when said cartridge holder is rotated with respect to said dose setting mechanism so that said spindle abuts a first surface of said bung.

7. A dose setting mechanism for priming a drug delivery device, said drug delivery device including: a coupling part, a spindle nut, and a cartridge holder holding a cartridge comprising a moveable bung, said dose setting mechanism configured to be coupled to said cartridge holder, and said dose setting mechanism comprising:
   a dose dial sleeve, said coupling part configured to connect said cartridge holder to said dose dial sleeve; and
   a spindle, said spindle nut rotationally coupled to said coupling part and configured to couple said cartridge holder to said spindle of said dose setting mechanism such that when said cartridge holder is rotated with respect to said dose setting mechanism, said spindle nut is rotated along with said cartridge holder with respect to said dose setting mechanism and at a same time driven in a distal direction with respect to said dose setting mechanism,
   wherein said coupling part is configured to unlock said dose dial sleeve so that said dose dial sleeve becomes free to rotate to set a dose, and
   wherein said dose setting mechanism is configured such that said cartridge holder must be rotated with respect to said dose setting mechanism before said dose can be set with said dose setting mechanism.

8. The dose setting mechanism of claim 7 wherein said dose setting mechanism is configured such that when said cartridge holder is rotated with respect to said dose setting mechanism, said spindle nut rotates and advances said spindle axially in the distal direction with respect to the dose setting mechanism such that said spindle nut moves said spindle into an abutting engagement with said bung.

9. The dose setting mechanism of claim 7 wherein said coupling part comprises a thin metal pressing.

10. The dose setting mechanism of claim 7 wherein said coupling part comprises a rigid coupling component.

11. The dose setting mechanism of claim 7 wherein said dose setting mechanism further comprises at least one flexible locking element, and
   wherein when said cartridge holder is rotated with respect to said dose setting mechanism, said coupling part also rotates to thereby release said at least one flexible locking element and allow said dose dial sleeve to rotate and allow a user of said drug delivery device to set a dose.

12. The dose setting mechanism of claim 7 wherein said spindle nut comprises a plurality of helical ramps, said plurality of helical ramps configured to drive said spindle nut in said distal direction with respect to the dose setting mechanism when said cartridge holder is rotated with respect to the dose setting mechanism so that said spindle abuts a first surface of said bung.

13. The dose setting mechanism of claim 7 wherein said dose setting mechanism is configured such that rotation of said cartridge holder from a first position to a second position primes said drug delivery device.

14. The dose setting mechanism of claim 13 wherein said dose setting mechanism is configured such that after said cartridge holder is rotated from the first position to the second position, said cartridge holder is rotationally locked to said dose setting mechanism.

15. The dose setting mechanism of claim 14 wherein said cartridge holder is configured to be rotationally locked to said dose setting mechanism by way of a one way, non-return detent feature.

16. The dose setting mechanism of claim 7 wherein said dose setting mechanism includes, along an outer surface of the dose setting mechanism, a marking indicating an unprimed state and a marking indicating a primed stated, and
wherein said cartridge holder includes a positional indicator that indicates a relative position of a cartridge housing with respect to the outer surface of the dose setting mechanism.

* * * * *